United States Patent [19]
Cahoon et al.

[11] Patent Number: 5,888,790
[45] Date of Patent: Mar. 30, 1999

[54] MODIFIED ACYL-ACP DESATURASE

[75] Inventors: Edgar B. Cahoon; John Shanklin, both of Shoreham, N.Y.; Ylva Lindqvist; Gunter Schneider, both of Järfälla, Sweden

[73] Assignee: Brookhaven Science Associates LLC, Upton, N.Y.

[21] Appl. No.: 853,979

[22] Filed: May 9, 1997

Related U.S. Application Data

[63] Continuation-in-part of Ser. No. 689,823, Aug. 14, 1996, Pat. No. 5,705,391.

[51] Int. Cl.⁶ .............................. C12N 9/02; C12N 15/00
[52] U.S. Cl. ..................................... 435/172.3; 435/172.1; 435/189
[58] Field of Search ............................. 435/172.1, 172.3, 435/189

[56] References Cited

U.S. PATENT DOCUMENTS

| | | | |
|---|---|---|---|
| 5,443,974 | 8/1995 | Hitz et al. ............................. | 435/172.3 |
| 5,614,400 | 3/1997 | Cahoon et al. ....................... | 435/172.3 |
| 5,654,402 | 8/1997 | Cahoon et al. ......................... | 530/377 |
| 5,705,391 | 1/1998 | Cahoon et al. .......................... | 435/419 |

*Primary Examiner*—Rebecca E. Prouty
*Assistant Examiner*—Einar Stole
*Attorney, Agent, or Firm*—Margaret C. Bogosian

[57] ABSTRACT

Disclosed is a method for modifying the chain length and double bond positional specificities of a soluble plant fatty acid desaturase. More specifically, the method involves modifying amino acid contact residues in the substrate binding channel of the soluble fatty acid desaturase which contact the fatty acid. Specifically disclosed is the modification of an acyl-ACP desaturase. Amino acid contact residues which lie within the substrate binding channel are identified, and subsequently replaced with different residues to effect the modification of activity.

20 Claims, 2 Drawing Sheets

Specific activities of wild-type and mutant $\Delta^6$-16:0-ACP desaturases

| Enzyme | Specific Activity | | | | Ratio of Total Specific Activity |
|---|---|---|---|---|---|
| | 16:0-ACP | | 18:0-ACP | | |
| | $\Delta^6$ | $\Delta^9$ | $\Delta^6$ | $\Delta^9$ | 16:0-ACP:18-0-ACP |
| | (nmole/min/mg protein) | | | | |
| $\Delta^6$-16:0-ACP Desaturase (wild type) | 99.7 | n.d. [a] | 10.6 (2:1) [b] | 5.3 | 6:1 |
| Chimera 4 ($\Delta^6/\Delta^9{}_{178-207}/\Delta^6$) | 13.4 (3:1) | 4.0 | 14.7 (1:1) | 17.1 | 1:2 |
| Chimera 5 ($\Delta^6/\Delta^9{}_{178-202}/\Delta^6$) | 250 | n.d. | 267 | trace [c] | 1:1 |
| A181T/A188G/Y189F/ S205N/L206T/G207A [d] | 34.0 (3:1) | 12.3 | 34.5 (1:2) | 57.7 | 1:2 |
| A188G/Y189F | 37.1 | n.d. | 37.0 | trace | 1:1 |
| A181T/A200F | 149 | n.d. | 3.1 [e] (1:14) | 43.6 | 3:1 |
| A181T/A200F/S205N/ L206T/G207A | 18.7 (17:1) | 1.1 [e] | n.d. | 72.6 | 1:4 |

[a] n.d. = not detected.

[b] x:y is the ratio of $\Delta^6$:$\Delta^9$ activity with given substrate.

[c] trace = ≤2% of the total activity with given substrate.

[d] Amino acid numbering is with respect to the sequence of the $\Delta^9$-18:0-ACP desaturase.

[e] Identification based on mobility of methyl ester derivative on argentation TLC plates.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:1:

ATGGATCCTG GCACGGATAA CAACCCGTAC    30

( 2 ) INFORMATION FOR SEQ ID NO:2:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:2:

ACGAGGTGTA GATAAATCCG AGGTACGGGT TGTTATCCG    39

( 2 ) INFORMATION FOR SEQ ID NO:3:

( i ) SEQUENCE CHARACTERISTICS:
  ( A ) LENGTH: 31 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:3:

TATCTACACC TCGTATCAGG AGAGGGCGAC A    31

( 2 ) INFORMATION FOR SEQ ID NO:4:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:4:

TTGAATTCCA TGGGAAATCG CTGTCGCCCT CTCCTG    36

( 2 ) INFORMATION FOR SEQ ID NO:5:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear (i i) MOLECULE TYPE: DNA (genomic)

(x i) SEQUENCE DESCRIPTION: SEQ ID NO:5:

ATGGATCCTG GCGCGGATAA CAACCCGTAC 30

(2) INFORMATION FOR SEQ ID NO:6:

(i) SEQUENCE CHARACTERISTICS:
  (A) LENGTH: 39 base pairs
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO:6:

ACGAGGTGTA GATATATGCG AGGTACGGGT TGTTATCCG 39

(2) INFORMATION FOR SEQ ID NO:7:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO:7:

TTGAATTCCA TGGGAAATGA ATGTCGCCCT CTCCTG 36

(2) INFORMATION FOR SEQ ID NO:8:

(i) SEQUENCE CHARACTERISTICS:
  (A) LENGTH: 38 base pairs
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO:8:

TTTCCATGGG AACACGGCTC GGCTAGCGAG GCAGAAGG 38

(2) INFORMATION FOR SEQ ID NO:9:

(i) SEQUENCE CHARACTERISTICS:
  (A) LENGTH: 26 base pairs
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO:9:

CCGAACTCCA TCGAAGGTAT TCAGCA 26

(2) INFORMATION FOR SEQ ID NO:10:

(i) SEQUENCE CHARACTERISTICS:
  (A) LENGTH: 26 base pairs
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO:10:

-continued

```
TGCTGAATAC  CTTCGATGGA  GTTCGG                                              26
```

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
GCAAAAGCCA  AAACGGTACC  ATCAGGATCA                                          30
```

( 2 ) INFORMATION FOR SEQ ID NO:12:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
GGACTGTTTT  CTGTCCGAAT  ATCCATTCCT  GAACCA                                  36
```

( 2 ) INFORMATION FOR SEQ ID NO:13:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
TGGTTCAGGA  ATGGATATTC  GGACAGAAAA  CAGTCC                                  36
```

( 2 ) INFORMATION FOR SEQ ID NO:14:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Asp  Pro  Gly  Ala  Asp  Asn  Asn  Pro  Tyr  Leu  Ala  Tyr  Ile  Tyr  Thr  Ser
 1              5                        10                       15

Tyr  Gln  Glu  Arg  Ala  Thr  Ala  Ile  Ser  His  Gly  Ser  Leu  Gly
              20                       25                       30
```

MODIFIED ACYL-ACP DESATURASE

RELATED APPLICATIONS

The subject patent application is a continuation-in-part of U.S. application Ser. No. 08/689,823, filed Aug. 14, 1996, now U.S. Pat. No. 5,705,391.

This invention was made with Government support under contract number DE-AC02-76CH00016, awarded by the U.S. Department of Energy. The Government has certain rights in the invention.

BACKGROUND OF THE INVENTION

Fatty acid biosynthesis in higher plants has recently attracted increased interest because of the possible use of plant oils as renewable sources for reduced carbon. In plants, fatty acid biosynthesis occurs in the chloroplasts of green tissue or in the plastids of nonphotosynthetic tissues. The primary products in most plants are acyl carrier protein (ACP) esters of the saturated palmitic and stearic acids.

$\Delta^9$ stearoyl-acyl carrier protein desaturase ($\Delta^9$ desaturase) is a plastid localized non-membrane bound soluble desaturase that introduces the first double bond into saturated fatty acids (resulting in the corresponding mono-unsaturated fatty acids). Recently, several related soluble desaturases have been identified in the seed tissues of various plants that possess fatty acids with unusual double bond positions. Members of this class of soluble desaturases are specific for a particular substrate chain length and introduce the double bond between specific carbon atoms by counting from the carboxyl end of the fatty acid; for instance, the $\Delta^9$ desaturase is specific for stearoyl-ACP, and introduces a double bond between carbon 9 and 10. Initial desaturation reactions in animals and fungi, and subsequent desaturation reactions in plants, are mediated by a distinct class of fatty acid desaturases that are integral membrane proteins. Since most plants lack other desaturases that act on the 18:0 level, the ratio of saturated to unsaturated fatty acids in higher plants is mainly controlled by enzymes which catalyze the conversion of saturated to mono-unsaturated fatty acids. $\Delta^9$ desaturase cDNA encode precursor proteins containing an N-terminal transit peptide for targeting to the plastid. For safflower and castor, the 33 residue transit peptide is cleaved off to yield a 363 amino acid mature desaturase polypeptide with an apparent molecular weight of 37 kDa per subunit by SDS-PAGE. The enzyme occurs as dimers of approximately 70 kDa. The enzymatic reaction requires molecular oxygen, NAD(P)H, NAD(P)H ferredoxin oxido-reductase and ferredoxin.

Previous studies have shown that both soluble and membrane-bound $\Delta^9$ desaturases require non-haem iron for catalytic activity. More recently, spectroscopic analysis and amino acid sequence comparisons have established that the $\Delta^9$ desaturase contains a diiron cluster. This class of diiron proteins is characterized by two occurrences of the sequence motif E-X-X-H, spaced by approximately 100 amino acids, and includes the R2 subunit of ribonucleotide reductase and a methane monooxygenase hydroxylase component. A greater understanding of the catalytic mechanism of the acyl-ACP desaturase enzymes may enable the exploitation of such enzymes in the manufacture of plant seed oil.

SUMMARY OF THE INVENTION

The subjection invention relates to a method for modifying the chain length and double bond positional specificities of a soluble plant fatty acid desaturase. More specifically, the method involves modifying amino acid contact residues in the substrate binding channel of the soluble fatty acid desaturase which contact the fatty acid. In preferred embodiments, the soluble plant fatty acid desaturase is an acyl-ACP desaturase.

Amino acid contact residues which lie within the substrate binding channel are identified, for example, by first providing the primary amino acid sequence of the acyl-ACP desaturase. Many such sequences are known, and others can be determined through the application of routine experimentation. Such amino acid sequences are then aligned with the primary amino acid sequence of the *Ricinus communes* $\Delta^9$ desaturase for maximum sequence conservation. A 3-dimensional model for the acyl-ACP desaturase is then constructed based on the sequence conservation with the *Ricinus communis* $\Delta^9$ desaturase. Amino acid contact residues within the substrate binding channel of the modeled structure are then identified. A mutant acyl-ACP desaturase having modified chain length and double bond positional specificities is then generated by replacing one or more of the amino acid contact residues with another amino acid residue.

In another aspect, the present invention relates to a mutant acyl-ACP desaturase which is characterized by the ability to catalyze desaturation of a first fatty acid and a second fatty acid, the first and second fatty acids differing in their chain length. This mutant is further characterized by the ability to desaturate both the first and second fatty acids at rates differing by no more than about 4-fold.

The invention also relates to compositions such as a nucleic acid sequences and expression vectors encoding a mutant acyl-ACP desaturase of the type described above. Other compositions of the present invention include cells transformed with such expression vectors. In another aspect the present invention relates to chimeric acyl-ACP desaturases having modified chain length and double bond positional specificities.

BRIEF DESCRIPTION OF THE DRAWINGS

FIG. 1 summarizes the specific activities of wild-type and mutant acyl-ACP desaturases.

DETAILED DESCRIPTION OF THE INVENTION

Figure 2:
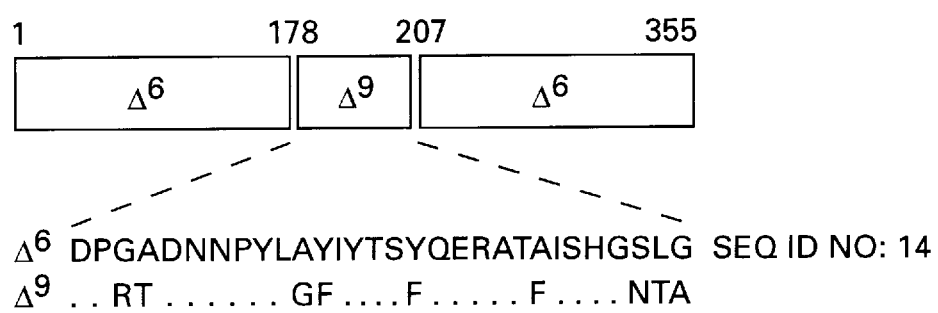
FIG. 2 is a linear representation of a chimera of the present invention and a sequence comparison of amino acids 178–207 of the mature $\Delta^6$-16:0-($\Delta^6$) and $\Delta^9$-18:0-($\Delta^9$) ACP desaturases from *T. alata*. Numbers in italics refer to amino acid positions in the mature $\Delta^9$-18:0-ACP desaturase, and non-italicized numbers indicate amino acid positions in the mature $\Delta^6$-16:0-ACP desaturase.

The present invention is based in part on the identification of the substrate binding groove, and critical contact residues which line the groove in a $\Delta^9$ acyl-ACP desaturase. In addition, the invention involves assaying the effects of logic based site-directed mutations. Prior to this work, the relative location of the substrate binding channel of acyl-ACP desaturases, and critical substrate contact residues, had been unknown.

Acyl-ACP desaturases are highly conserved, with >70% amino acid sequence homology found between members of different families such as the $\Delta^4$, $\Delta^6$ and $\Delta^9$ acyl-ACP desaturases. Each of these desaturases is known to catalyze the formation of double bonds between carbon atoms of the same or similar substrate fatty acids. The primary difference between the various acyl-ACP desaturase activities is the location of the carbon atoms within the substrate fatty acids that are to be desaturated.

Amino acid sequence conservation is even greater within a particular family of acyl-ACP desaturases such as $\Delta^9$. Based on the present disclosure one of skill in the art would predict that contact residues within the substrate binding channel of all $\Delta^9$-acyl-ACP desaturase members are substantially similar, if not identical, to those identified in the $\Delta^9$-acyl-ACP desaturase described in Example 1 below.

The high degree of amino acid sequence homology within a family of acyl-ACP desaturases which catalyze the same enzyme reactions, and amino sequence homology between families of acyl-ACP desaturases that catalyze different enzyme reactions suggests that certain portions of the enzymes will exhibit similar tertiary structures. This is consistent with the finding for other molecules, such as antibodies, where conservation of amino acid residue homology is normally greatest within those amino acids involved in maintaining the functional structure of the molecule of question.

One such structural region in acyl-ACP desaturases which is conserved between the different acyl-ACP desaturases is the substrate binding channel described in the Exemplification section which follows. The substrate binding channel described below exhibits an architecture providing near perfect accommodation for the fatty acid substrate. If not unprecedented, such an exquisite fit is extremely uncommon.

The fact that this substrate binding channel is highly conserved can be confirmed by aligning for maximum identity (by conventional techniques) the amino acid sequences of members of other acyl-ACP desaturase families with that of the Castor (i.e., *Ricinus communis*) $\Delta^9$ acyl-ACP desaturase described in Example 1 below. The deduced amino acid sequence of this Castor protein was reported by Shanklin and Somerville (*Proc. Natl. Acad. Sci. USA* 88:2510 (1991)). Following this alignment, a 3-dimensional model can be generated which will reveal the characteristic substrate binding channel. Among the acyl-ACP desaturase sequences from various plant sources determined to date, the following are available through GenBank (accession codes shown in square brackets): [BRSACP] *B. rapa*; [CAHSACPD] *C. tinctorius*; [SMMSCPD] *Simmondsia chinensis*; [SOACCPDS] *S. oleracea*; [SSMSACPD] sesame plant source; [TAU07597] *Thunbergia alata* (clone pTAD2 $\Delta^9$); [TAU07605] *Thunbergia alata* (clone pTAD3 $\Delta^9$); [ATSTACPDS] *A. thaliana*; [BNAACPDES] *B. napus*; [BNSACPD] *B. napus*; [GHSACPDES] *G. hinsutum*; [LUSACPDE] *L. usitatissimum*; [RCSTEA] *R. communis*; [SOYSACPD] Glycine max; [SSMSACPDA] sesame plant; [SSMSACPDB] sesame plant; [TAU07552] *Thunbergia alata* (clone pTAD1 $\Delta^9$).

By studying the results of the molecular modeling for any of the acyl-ACP desaturases, as was done below in connection with the Castor $\Delta^9$ acyl-ACP desaturase, amino acid residues within the substrate binding channel which are oriented such that they will be in very close proximity to the fatty acid substrate can be identified. Such residues are referred to as "contact residues". As revealed through the description of the experimental work below, the modification of a contact residue (and in some cases, other residues as exemplified by the chimeras of Examples 2 and 3) can alter the chain-length and double bond positional specificities of an acyl-ACP desaturase.

For example, as shown in Examples 2 and 3 below, a chimera was produced wherein amino acids 172–202 of $\Delta^6$-16:0-ACP desaturase were replaced by amino acids 178–207 of $\Delta^9$-18:0-ACP desaturase. This led to the introduction of 9 novel amino acids into the substrate binding channel of the $\Delta^6$-16:0-ACP desaturase that differed from the amino acids at the corresponding positions in the wild-type $\Delta^6$-16:0-ACP desaturase. The chimera was not only able to desaturate the 16:0 fatty acid the wild type functioned best with, but was also able to desaturate an 18:0 at both the $\Delta^6$ and $\Delta^9$ positions at equivalent levels.

The fact that the amino acid contact residues in the substrate binding channel of an acyl-ACP desaturase play such a critical role in determining chain length and double bond positional specificity offers an opportunity for the rational design of mutant acyl-ACP desaturases which have unique and useful properties.

Such novel mutant molecules can be designed, for example, by first identifying contact residues within the substrate binding channel (as described above through alignment with the Castor $\Delta^9$ amino acid sequence followed by 3-dimensional modelling). Specific point mutations can then be introduced into the acyl-ACP desaturase molecule of interest. This is most conveniently done at the genetic level using common techniques such as site-directed mutagenesis.

A variety of site-directed mutagenic techniques can be applied to introduce a specific amino acid codon change (i.e., substitution) within such DNAs. Care must be exercised in selecting a residue to be substituted for an existing contact residue in the substrate binding channel of a wild-type acyl-ACP desaturase. It is generally important in initial studies, for example, to select residues for substitution which do not differ radically with respect to side chain size or charge. For example, if a glycine contact residue (characterized by its compact aliphatic side chain) is identified within the substrate binding channel, the substitution of an amino acid residue such as arginine (characterized by the presence of a bulky, basic side chain) could serve to block entry of the fatty acid substrate into the substrate binding channel through stearic hindrance. In general, initial amino acid substitutions for contact residues should be made using amino acids having similar charge characteristics with relatively small differences in terms of side chain bulk. This having been said, it is certainly possible that the substitution of an amino acid having radically different properties from a wild-type contact residue may yield a particularly useful mutant acyl-ACP desaturase. Such a molecule would be encompassed by the present invention. The brief discussion of substitution strategy given above is intended only to serves as a guide to the incremental modification of an acyl-ACP desaturase.

Thus, it is the knowledge of the identity of the contact residues within an acyl-ACP desaturase that allow one skilled in the art to make modifications to the enzyme that can alter the chain-length and double bond positional specificities of the enzyme without inhibiting its ability to carry out enzyme catalysis. This knowledge, in turn, is dependent upon the ability of one of skill in the art to identify the substrate binding channel, and generate a 3-dimensional model.

As already discussed, the nucleotide sequences of many acyl-ACP desaturase have been reported. Furthermore, given their high degree of conservation, routine nucleic acid hybridization experiments carried out using DNA isolated from a plant of interest, would be likely to yield DNA encoding additional acyl-ACP desaturases.

Further, as indicated above, one of skill in the art would predict that within the $\Delta^9$ acyl-ACP desaturase family, amino acid contact residues within the substrate binding groove would be substantially similar, if not identical. The amino acid contact residues identified by the X-ray crystallographic work described in Example 1 are residues M114, L115, T117, L118, P179, T181, G188 and F189. That modification of these residues in a $\Delta^9$ acyl-ACP desaturase does, in fact, alter the chain-length and double bond positional specifics of the enzyme was confirmed in the experiments described in Example 2. More specifically preliminary experimental work has revealed that a single amino acid substitution at position 118 (Leu to Phe) in Castor $\Delta^9$ acyl-ACP desaturase results in an approximately 10-fold increase in its activity with 16:0-ACP. Thus, one amino acid substitution at a contact residue position can generate an acyl-ACP desaturase with novel and useful properties.

Prior to this invention, the only source of variant acyl-ACP desaturases was plant tissue which synthesizes unusual isomers of monounsaturated fatty acids. For example, the $\Delta^4$-16:0-ACP desaturase was derived from seed endosperm of coriander, a tissue that produces large amounts of petroselinic acid (18:1$\Delta^6$), an unusual monounsaturated fatty acid. The present invention enables the design and production of new types of acyl-ACP desaturases without the need for isolating cDNAs for these enzymes from plant sources. In addition, the present invention enables the design of acyl-ACP desaturases that can catalyze the synthesis of economically valuable monounsaturated fatty acids that are not found in nature.

In a more specific example, this invention offers an alternative means of petroselinic acid production in plants. This fatty acid has a number of potential industrial and nutritional uses. The only known pathway of petroselinic acid formation in plants involves the $\Delta^4$ desaturation of 16:0-ACP followed by elongation of the resulting 16:1$\Delta^4$-ACP to form 18:1$\Delta^6$ (or petroselinoyl)-ACP. This pathway requires, among other things, a novel acyl-ACP desaturase and a specific acyl-ACP elongation system. Among the mutant desaturases described below are enzymes that can catalyze the $\Delta^6$ desaturation of 18:0-ACP to form petrosinoyl-ACP. Such enzymes are useful for the production of petroselinic acid in transgenic crop plants without the need to transfer additional genes for the 16:1$\Delta^4$-ACP elongation pathway. This pathway is a current limitation in efforts to produce petroselinic acid in transgenic crop plants through the introduction of the gene for $\Delta^4$-16:0-ACP desaturase.

Thus, mutants generated by altering the identity of one or more contact residues in the substrate binding channel can be used to generate acyl-ACP desaturases having unique functional characteristics. Such enzymes can be used, for example, to generate vegetable oils rich in monounsaturated fatty acids. Such vegetable oils are important in human nutrition and can be used as renewable sources of industrial chemicals. In addition, the ability to manipulate chain length preferences and double bond positions of these molecules offers a way to manipulate physical properties and commercial uses of conventional plant oils. In addition, the development of transgenic crops capable of producing unusual types of monounsaturated fatty acids can be exploited based on the present disclosure.

Mutants disclosed in the Example 2 below exhibit certain unique properties. For example, wild-type acyl-ACP desaturases tend to exhibit very strong preferences for a particular chain length fatty acid and bond position. However, in the experiments described below, amino acid substitutions for contact residues within the substrate binding channel have been shown to modify this preference. For example, chimeric mutants are described which exhibit the ability to catalyze desaturation of substrates of different lengths (e.g., 16:0 and 18:0) at rates differing by no more than about 4-fold.

Nucleic acid sequences encoding these mutant acyl-ACP desaturases can be used to express the mutant enzyme using recombinant DNA techniques. For example, when cloned in an appropriate expression vector, the mutant acyl-ACP desaturase can be expressed in a variety of cell types including, for example, prokaryotic and eukaryotic cells.

Prokaryotic expression vectors are useful, for example, for the preparation of large quantities of the protein encoded by the DNA sequence of interest. Following purification by conventional methods, this protein can be used to desaturate a fatty acid. In addition, for some applications a crude lysate of such a prokaryotic cell culture may be useful.

Eukaryotic expression vectors are useful when the addition of carbohydrate side chains (i.e., glycosylation) to the protein is important. The carbohydrate side chains affect the activity of a protein in several ways. For example, it is known that certain proteins are inactive in their non-glycosylated state. In addition, the ability of a non-glycosylated protein to form a complex with other proteins (e.g., antibodies or regulatory molecules) can be adversely affected in the absence of glycosylation. Following purification by conventional methods, an acyl-ACP desaturase mutant expressed in a eukaryotic system (e.g., the baculovirus expression system) can be used to modify the chain-length and double bond position of a fatty acid. This protein can also be used as part of a crude lysate in many circumstances.

The mutant acyl-ACP desaturases can also be cloned into a plant expression vector. These vectors allow the production of a desired protein product, for example the mutant acyl-ACP desaturase, within the milieu of the plant cell within which the substrate fatty acid reside. By producing the enzyme in situ, modification of the product can occur prior to harvest, allowing rapid purification of the desired fatty acid with the appropriate double bond position, and without the need of costly manufacturing steps. In some instances, more than one mutant acyl-ACP desaturase may be desired in a particular transgenic plant to produce fatty acids with double bonds at multiple positions. Plants are also easy to cultivate, and grow in large quantity. This protein can also be used as part of a crude lysate in many circumstances.

EXEMPLIFICATION

EXAMPLE 1

Results and Discussion

Electron density map and quality of the model

The three-dimensional structure of recombinant homodimeric $\Delta^9$ stearoyl-acyl carrier protein desaturase, the archetype of the soluble plant fatty acid desaturases that convert saturated to unsaturated fatty acids, has been determined by protein crystallographic methods to a resolution of 2.4 Å. The six-fold averaged electron density for the main chain and side chains for most of the polypeptide chain is well defined. Exceptions are the first 18 residues at the N-terminus, which are not defined in electron density and might be flexible in the crystal lattice. Residues 336–347 located in a loop region, are very poorly defined in the electron density maps and it is also in this part of the protein structure where the largest deviations from the noncrystallographic symmetry are found. The overall residue by residue real space correlation (Br subunit and the six-fold averaged 2Fo-Fc electron density map is 0.76). Criteria such as crystallographic R- factor (R=22.0%, $R_{free}$=28.5% with noncrystallographic symmetry restraints), good stereochemistry of the model (bond length rms of 0.008 Å), Ramachandran plot (only one outlier from the allowed regions per subunit, except glycine residues) and the observed hydrogen bonding pattern all indicate that the chain tracing for fatty acid desaturase is correct. There is very clear density for the peptide oxygen of Lys 262, the residue with a disallowed main chain conformation. The high average β-factor suggest that the molecule is flexible. The most ordered parts of the molecule are areas involved in dimer and hexamer interactions whereas surface loops often have very high β-factors.

The major binding sites for the $Au(CN)_2$- ions in the derivatized desaturase crystals are found close to the side chains of K56 and C61 at the surface of the molecule. One of the minor sites is internal, between the side chains of H203 and C222, and the second minor site is in the area of where the N-terminus of the chain probably is situated.

The overall shape of the $\Delta^9$ desaturase subunit is a compact cylinder of dimensions 35×35×50 with an accessible surface area of 16773. Besides a β-hairpin-loop at the very C-terminus of the chain, the subunit is mainly composed of helical secondary structures folded into one large domain. Nine of the total eleven α-helices form an antiparallel helical bundle.

The N-terminal part of the chain is disordered, no electron density is observed for the first 18 residues. The next 15 residues lack secondary structure and form an extended chain packing along the helix bundle with few specific interactions to stabilize its structure. The first helix, α1, composed of 23 residues, starts and ends in $3_{10}$-conformation and is very bent so that its first half forms a cap at one end of the bundle and its second part is the first helix of the bundle. The chain continues in the same direction forming hydrogen-bonded turns and a $3_{10}$-helix. The cap at the other end of the bundle is formed by helices α2 and α$\Delta^9$ and the C-terminal-hairpin. Four of these helices, α3, α4, α6 and α7, which are very long, 28, 29, 30 and 31 residues respectively, contribute ligands to the diiron center.

Although α3 has a break in the helical structure in the middle at residue 107–108, α3 and α4 are symmetrical to α6 and α7 and can be superimposed with an r.m.s deviation of 1.39 Å for 44 residues. Such a superposition also aligns the iron atoms to within 1.0 Å. The corresponding sequence alignments show that there is little sequence conservation besides the residues involved in binding the iron cluster. This superposition also orients the cap part of α1 onto α2. The connections between these helices also approximately superimpose although there is no detailed structural similarity. Between α3b and α4 there is a protruding loop structure stabilized by several hydrogen-bonded turns. Helices α5, α8, α10 and α11, which is very curved, complete the bundle.

There are a large number of salt bridges, 25, excluding those interacting with the iron ions, within the subunit. This corresponds to 0.069 ion pairs per residue, higher than the average number of ion pairs per residue, 0.04, derived from a survey of 38 high resolution protein structures. Seven of the salt bridges in $\Delta^9$ desaturase are involved in inter-helix interactions within the bundle, securing the correct mutual packing and in some instances correct orientation of the iron-ligands. Eight pairs make intra-helix contacts and three of the remaining are involved in anchoring the turns between bundle-helices. Three pairs are involved in contacts to the $3_{10}$-helix and the loop after α8. A peculiar feature of the $\Delta^9$ desaturase subunit is a rather flat surface formed by helices α1, α6, α7, α10 and α11. This surface is not involved in subunit-subunit contacts in the dimer but is accessible from the solution.

The dimer

The subunit-subunit interface in the dimer buries a surface area of 5826 Å$^2$ per dimer, 17.4% of the dimer area. These two fold interactions include extensive contacts between helices in the bundles; from α3b to the same helix in the second subunit, between α4 and α5, and over α2 and α4 to the corresponding helices in the other subunit. There are also many contacts between the protruding loop between α3b and α4 and the N-terminal, α3b, and α5. In addition, residues in the connection between α1 and α2 make contacts to α4 and α5 in the second subunit. There are three charged interactions in the dimer contact area, two of these involve residues from α5. The diiron centers are separated by more than 23 Å in the dimer and have no direct contacts to each other.

Noncrystallographic symmetry and crystal packing

The crystal asymmetric unit contains three $\Delta^9$ desaturase dimers. In these dimers the subunits are related by two-fold noncrystallographic axes which for one of the dimers is parallel to one of the crystallographic two fold-axes. At right angles to this, parallel to a, there is a three-fold noncrystallographic screw-axis relating the three dimers. The translation is one third of the length of a, i.e. it is a local 31 axis. The contacts between the dimers are not extensive, of the same order as other crystal contacts and the influence of crystal contacts on the structure seems to be minor as judged from the small deviations in non-crystallographic symmetry observed. The largest deviations are obtained for residues 336–347 where R336, E347 and/or K346 make crystal contacts, including salt bridges, in some of the subunits. The electron density in this area is weak as mentioned above. Another area with deviations from the noncrystallographic symmetry includes residues 19 to 50 which are wrapped around the subunit and also are making different loose crystal contacts in the subunits. The packing of subunits corresponding to one asymmetric unit, viewed along the three-fold and one of the two-fold axes.

The diiron center

Previous studies have shown that $\Delta^9$ desaturase contains four iron atoms per dimer and optical and Mössbauer spectroscopy indicated that these iron ions comprise a diiron-oxo-clusters. Diiron-oxo-clusters have now been identified in a wide variety of proteins that perform both catalytic and non-catalytic functions. They contain two iron atoms connected by either an oxo- or hydroxo-bridging ligand and have been classified based on differing primary sequence motifs providing the cluster ligands, and upon structural differences elucidated by X-ray crystallography. Four classes have been described, one containing haemerythrin and myohemerythrin, a second containing the R2 subunit of ribonucleotide reductase, bacterial hydrocarbon hydroxylases, and the $\Delta^9$ desaturase, a third containing rubrerythrin, and a fourth containing Fe(III)—Zn(II) purple acid phosphatase (Strmammalian Fe(II)—Fe(II) acid phosphatases). In addition to these soluble proteins, there is a distinct class of functionally related integral membrane proteins including fatty acid desaturases and hydrocarbon hydroxylases which contain oxygen-activated non-heme ironcenters, which have yet to be structurally characterized.

The crystal structure of $\Delta^9$ desaturase reveals that the enzyme belongs to class II diiron proteins and that it contains a metal cluster. The distance between the iron ions is 4.2 Å and the coordination geometry of the iron ions is a distorted octahedron where one of ligand positions is unoccupied. The structure of the cluster is highly symmetric. E143 from α4 and E229 from α7 both act as bridging ligands. E105 from α3a is a bidentoate ligand to one iron ion and correspondingly, E196 from α6 is a bidentate ligand to the second iron ion. Each iron ion is also ligated by a nitrogen atom, Nδ1 in H146 from α4 and H232 from α7 respectively. The orientation of the iron ligands is in some cases maintained by side chain hydrogen bonds; E105 interacts with H203, E143 with atom Nε1 in W139, Nε2 in H146 with the side chain of D228 which in turn interacts with the side chains of R145 and W62, Nε2 in H232 with the side chain of E143 which in turn interacts with the side chain of R231. Further away from one of the iron ions is found atom Nε1 in W139 which might be considered to be a second shell ligand. In the vicinity of the iron cluster, there is electron density corresponding to a solvent molecule. Its distances to the iron ions are 3.2 and 3.4 Å, respectively and it is therefore not part of the first coordination shell of the metal center.

Form of the desaturase in the crystal structure

The presence of a Δ-oxo bridged diiron cluster in the diferric state of $\Delta^9$ desaturase has been unambiguously demonstrated using Mössbauer and resonance Raman spectroscopy. It is therefore surprising, that a μ-oxo bridge was not observed in the electron density map of $\Delta^9$ desaturase because the enzyme used for the experiments was in the oxidized state and no reducing agents were added to the mother liquor. In addition, the distance between the iron ions (4.2 Å) is longer than expected for a diiron cluster with an intact μ-oxo bridge. In the oxidized form of ribonucleotide reductase with the μ-oxo bridge present, the iron-iron distance is 3.3 Å. The geometry observed in $\Delta^9$ desaturase is strikingly similar to that seen in the reduced form of ribonucleotide reductase, where, upon chemical reduction of R2, the distance between the iron ions is increased to 3.8 Å, the μ-oxo bridge is lost and the ligand arrangement becomes very symmetric as shown by protein crystallography and Mössbauer spectroscopy. It can be suggested that exposure of the desaturase crystals to X-ray radiation results in photochemical reduction of the metal center which is accompanied by loss of the μ-oxo bridge and ligand rearrangement. Thus, the structure of the $\Delta^9$ desaturase presented here most likely represents the reduced form of the enzyme. The crystal structure of the $\Delta^9$ desaturase reveals a highly synmmetric ligand arrangement of the iron cluster in the diferrous form of the enzyme, in agreement with resonance Raman studies. Deviations in the symmetric ligand arrangement in the reduced state of the enzyme as suggested from previous temperature dependent Mössbauer data might be due to variations in bond lengths and bond angles in the two metal sites, too small to be observable in the electron density maps at the current resolution.

Active site and interactions with other proteins

The structure of $\Delta^9$ desaturase described here is very likely that of the diferrous form of the enzyme that results from interaction of $\Delta^9$ desaturase and ferredoxin in vivo. From the three-dimensional structure, two possible routes for electron transfer from the surface to the iron center can be postulated. One of these extends along the axis of the helix bundle and involves the structurally consecutive cluster of aromatic sidechains of W139, W135, Y236, F189, W132. The Nε1 atom of W139 is in rather close distance to one of the irons and the Nε1 atom of W132 points towards the surface of the subunit close to the protruding loop between α3b and α4. This loop and the cap-part of α1 could then form a possible interaction surface for the ferredoxin molecule. Another possible route for electron transfer from the surface to the iron center involves residues W62, D228 and H146 analogous to what has been suggested for R2. This pathway leads to the flat surface formed by helices α1,α6, α7, α10 and α11.

The solvent molecule bound in the vicinity of the iron center is located in a small, hydrophobic pocket and the closest amino acid side chains to this solvent molecule are T199 and W139. A similar cavity, with a Thr side chain at the equivalent position has been found in MMO and it has been suggested that this cavity could provide a suitable binding site for the oxygen molecule. The side chain of T213 in MMO has been implicated to be involved in oxygen activation in a similar manner as residue T252 in cytochrome P450.

Because the iron center is buried in the interior of the $\Delta^9$ desaturase, a substrate cleft lined with hydrophobic residues connecting the surface of the enzyme to the active site was expected to be identified. Indeed, a narrow, very deep channel can be found extending from the surface far into the protein. The channel passes the diiron center on the same side as the proposed oxygen binding site. At the bottom of this channel is found the side chain of L115 and the walls consist of residues W139, T192, Y111, M114, Y191, Q195, P266, T99, and T104. The channel then passes the iron cluster and continues towards the surface with residues Y292, M265, F279, and S283 at the narrow entrance of this cleft. The overall shape of the substrate channel which is bent at the position of the iron cluster facilitates binding of the product, oleoyl-ACP with cis configuration at the double bond.

After refinement, strong elongated electron density was found in the averaged 2Fo-Fc electron density maps in this channel which had not been assigned to solvent or protein atoms. Based on the shape of this density and the hydrophobic character of the pocket it can be inferred that this electron density may represent the hydrophobic acyl-tail of a β-octylglucoside molecule. The hydrocarbon tail of the octylglucoside would fit well in this density but the density corresponding to the sugar moiety is poorly defined. This putative octylglucoside molecule is oriented with its tail deep down in the hydrophobic pocket close to the diiron cluster and the carbohydrate moiety extending towards the surface. The weak electron density for this part of the molecule might indicate local disorder resulting from less specific interactions with the enzyme.

Modeling of a stearic acid in the presumed substrate binding pocket renders the C9 carbon atom at about 5.5 Å from one of the iron ions. This carbon atom, where the double bond will be formed, is also close to the small pocket with the bound solvent molecule, in fact the water molecule is bridging the distance between the C9 carbon of the substrate and the closest iron ion. In the active enzyme, this pocket is likely occupied by an oxygen molecule bound to one or both of the iron atoms. During catalysis, a peroxide radical could be generated capable of abstracting one of the hydrogen atoms at the C9 position of the fatty acid.

Comparison to other diiron proteins

A superposition of the structure of $\Delta^9$ desaturase on the three-dimensional structures of two other diiron proteins, the R2 subunit of ribonucleotide reductase from *Escherichia coli* and the α-subunit of MMO from *Methylococcus capsulate* shows that the overall structures are rather similar, with an r.m.s. fit of 1.90 Å for 144 Cα-atoms ($\Delta^9$ desaturase vs R2) and an r.m.s. fit of 1.98 Å for 117 equivalent Cα atoms ($\Delta^9$desaturase vs MMO). The folds are very similar, most of the α-helices, α1 to α8 and α10 have their counterpart in R2 and MMO. There are few conserved amino acids besides the iron ligands but there can be little doubt that these enzymes are evolutionary related.

There are significant differences in the structure of the iron centers in the three proteins. In general, the metal center in $\Delta^9$ desaturase is considerably more symmetrical than in the two other proteins. However, when compared to the structure of the reduced form of R2, the coordination geometries of the dinuclear iron center in $\Delta^9$ desaturase and R2 are more similar. The most significant difference is that in $\Delta^9$ desaturase, the terminal carboxylates E105 and E196, respectively act as bidentate ligands, whereas in R2, the equivalent side chains are monodentate ligands to the iron ions.

R2 is unique among these enzymes in that it forms a stable radical at position Y122. The corresponding residue in $\Delta^9$ desaturase is L150, located in the hydrophobic cluster making packing interactions in the four-helix bundle the iron cluster and no evidence is available which might indicate that this residue is required for catalytic activity.

There are very few amino acid residues which are conserved in all three enzymes. Among those are the ligands to the metal ions with the exception of E105 which is replaced by an aspartic acid in R2. The only other invariant residues are I225 and D228. Residue I225 is in the vicinity of the diiron cluster (closest distance 4.6 Å) on the opposite side of the substrate channel. The side chain is packed between H203, H146 and W62 in the three-dimensional structure, and a more detailed examination of its function has to await the results from site-directed mutagenesis studies. The other invariant protein residue in the three enzymes, D228, is part of an electron transfer pathway from the dinuclear iron center to the surface of the protein which has been suggested for R2. In R2, this pathway runs from one of the iron ions via the side chain of H118, D237 to W48, which is located at the surface of the protein. These residues are conserved in $\Delta^9$ desaturase and a similar pathway for electron transfer can be postulated including the structurally equivalent residues H146, D228 and W62 as mentioned before. Furthermore, a slightly modified pathway for electron transfer could also be suggested for MMO. In this case, the iron ligand (H147) and the aspartic acid residues (D242) are conserved, however the structure at the surface is different. Nevertheless, an aromatic side chain (Y67) at the surface is in the vicinity of the side chain of D242.

Most of the other residues conserved between $\Delta^9$ desaturase and R2 on one hand and $\Delta^9$ desaturase and MMO on the other hand are located at the surface of the protein, or involved in packing interactions. Conserved residues common between R2 and $\Delta^9$ desaturase in the proximity of the diiron site are residues W135 and W139. While W135 and W139 are strictly conserved in the desaturases, the corresponding residues W107 and W111 in R2 are not strictly conserved. Except for the T4 and E. coli protein, W135 is replaced by a phenylalanine or a tyrosine side chain. Similarly, W139 is replaced by a glutamine residue.

Materials and Methods

Enzyme purification and crystallization

Recombinant $\Delta^9$ desaturase was expressed in E. coli cells and purified as described previously (Fox et al., Biochemistry 33:127766 (1993)). Crystallization of the enzyme was achieved according to (Schneider, et al., J. Mol. Biol. 225:561, (1992)) with slight modifications. Enzyme samples were concentrated to 12–18 mg/ml. A 7.5 ml aliquot of protein solution was mixed with the same amount of the reservoir solution, placed on coverslips and allowed to equilibrate over 1 ml of the well solution at 20° C. The reservoir solution contained 0.08M cacodylate buffer pH 5.4, 200 mM Mg-acetate, 75 mM ammonium sulphate, 2 mM LiCl, 1 mM KCl, 0.2% β-octyl glucoside and 12–15% PEG 4000 as precipitant. The crystals were orthorhombic, space group $P2_12_12_1$, with cell dimensions a=82.2, b=147.8 and c=198.2 Å.

Data collection and preparation of heavy metal derivatives

Attempts to prepare heavy metal derivatives by soaking native crystals of the enzyme with solutions of various heavy metal salts in mother liquor were not very successful. Most soaking experiments resulted in crystal cracking or non-isomorphous crystals and only one useful heavy metal derivative could be prepared by soaking desaturase crystals in mother liquor containing 5 mM $KAu(CN)_2$ for one week. X-ray data from native and derivative crystals were collected on a UCSD multi-wire area detector system (Hamlin, Methods Enzymol. 114:416, (1985)) at the department of Molecular Biology, Uppsala. Measured frames were processed with MADNES (Pflugrath, MADNES: Munich area detector NE system, Users Guide, Cold Spring Harbor Laboratory, N.Y., U.S.A., (1987)). A second native data set was collected at beamline X12-C at NSLS, Department of Biology, Brookhaven National Laboratory. Data frames were collected as 10 oscillations using a MAR Research image plate. The data frames were processed with DENZO and scaled with SCALEPACK.

Phase determination, model building and crystallographic refinement

Most crystallographic calculations were done using the CCP4 program suite (Collaborative Computational Project, Number 4, Acta Crystallogr. D50:760, (1994)). The initial crystallographic analysis was carried out with the data sets collected on the multi-wire detector to 3.1 Å resolution. The difference Patterson map for the gold derivative was analyzed using RSPS (Knight, PhD thesis, Swedish University of Agricultural Sciences, Uppsala 1989). Two sites, related by a strong cross-peak in the difference Patterson map were used for calculation of difference Fourier maps and new sites were identified. Finally 6 main sites and 12 minor sites were found and the heavy metal parameters were refined using MLPHARE. From results of the rotation function calculations and the positions of the metal ions, the direction and position of the local symmetry operators, relating the six subunits of $\Delta^9$ desaturase in the asymmetric unit could be determined. Six-fold noncrystallographic symmetry averaging using the RAVE program (Jones, in CCP4 Study Weekend 1992: Molecular Replacement (Dodson, E. J., Gover, S. and Wolf, W., eds.) pp. 91–105, Daresbury Laboratory, Daresbury, UK,(1992)) and a spherical envelope, centered at the presumed position of one $\Delta^9$ desaturase subunit, was then used to refine the initial SIR phases. From an electron density map at low resolution, based on these phases, part of the central four-helix bundle, coordinating the diiron center and the iron atoms could be identified. The coordinates of the iron atoms were refined from the anomalous native data and new phases were calculated based on the Au-derivative and the anomalous contribution from the iron atoms. A new envelope for the subunit was made using MAMA (Kleywegt and Jones, Acta Cryst. D50:178 (1994)) by approximately orienting a subunit of R2 at the correct position for the helix-bundle.

After noncrystallographic averaging it was possible to build a starting model of the desaturase from the electron density map. Cycles of model building, refinement in XPLOR (Brunger, A., Acta Crystallogr. A45:50, (1989)) (Brunger, A., The X-PLOR manual, Yale University, New Haven, Conn., (1990)), redefinition of the envelope, refinement of the symmetry operators using IMP (Kleywegt and Jones, Acta Cryst. D50:171,(1994)) and averaging were performed until no new electron density appeared in the averaged maps. At this stage, one more loop which seemed to have a different structure in the subunits was built from the 2Fo-Fc-maps.

Crystallographic refinement was carried out with XPLOR, using the Engh and Huber force field (Engh and Huber, *Acta Crystallogr.* A47:392, (1991)) and noncrystallographic symmetry restraints. Due to the low resolution (3.1 Å) of the data set, an overall B-value was used. The model at this stage had a crystallographic R-factor of 26.7% with six-fold noncrystallographic symmetry restraints imposed in the refinement. At this stage of the refinement, a new native data set to 2.4 Å resolution collected at NSLS became available and refinement continued with this data set. The process of refinement was monitored by 2.5% of the reflections which were not included in the refinement but were used to calculate Rfree (Brunger, A., *Nature* 355:472 (1992)).

Even at the resolution of 2.4 Å the observation to parameter ratio is just about one and the refinement problem is ill determined. Therefore, during the whole refinement process, noncrystallographic symmetry restraints were employed in order to avoid over-fitting of the diffraction data. Only those parts of the structure were not restrained which from the averaged electron density maps were judged not to obey the noncrystallographic symmetry. This includes residues 19–50, 121–122, 127–129, 208–212, 241–253, 259–260, 308–319, 336–348 and some side chains. The electron density for some residues in the region 336–347 is so weak that their positions must be considered arbitrary and the occupancies for these atoms were therefore set to zero. Overall anisotropic refinement lowered the free R-factor by about 2%. At this stage, water molecules were added to the model. Individual B-factors were also refined but restrained by the noncrystallographic symmetry. The final model has a crystallographic R-factor of 22.0% (R free 28.5%). The r.m.s. deviations for the restrained Cα positions (263 atoms) of the subunit A to the corresponding parts of the other subunits are 0.06 and for all Cα atoms (345 atoms) 0.26, 0.23, 0.24, 0.32, 0.25, respectively.

The protein model was analyzed using the PEPFLIP and RSFIT options in O (Jones et al., *Acta crystalllogr.* A47:100, (1991)) and with the program PROCHECK (Laskowski et al., *J. Appl. Crystallogr.* 26:282, (1993)). The atomic coordinates will be deposited with the Brookhaven Protein Data Bank.

Structural comparisons

All structural superpositions were performed by least-squares methods using O (Jones et al., *Acta crystalllogr.* A47:100, (1991)) and were done pair wise. Superposition was done by selecting an initial set of equivalent Cα atoms consisting of four stretches of the polypeptide chain (about 10 residues each) from the four helices containing the ligands to the diiron center. This initial alignment was subsequently maximized by including all Cα atoms from the atomic models. Residues were considered structurally equivalent if they were within 3.8 from each other and within a consecutive stretch of more than three equivalent residues.

EXAMPLE 2

Results and Discussion

The approach of combining amino acid sequence elements from structurally related enzymes with different properties has proven effective in characterizing the substrate and positional specificities of fatty acid modifying enzymes such as mammalian lipoxygenases and plant acyl-ACP thioesterases. This approach was used here to identify the residues responsible for the differences in properties of a $\Delta^9$-18:0-ACP desaturase and a $\Delta^6$-16:0-ACP desaturase encoded by the *T. alata* cDNAs pTAD2 and pTAA$^4$, respectively. The mature polypetides encoded by these cDNAs share 65% amino acid sequence identity. Initially two chimeric mutants were constructed: (a) a first chimera contained the first 171 amino acids of the mature $\Delta^6$-16:0-ACP desaturase linked to the remaining 185 amino acids of the $\Delta^9$-18:0-ACP desaturase and (b) a second chimera contained the first 227 amino acids of the mature $\Delta^9$-18:0-ACP desaturase linked to the remaining 134 amino acids of the $\Delta^6$-16:0-ACP desaturase. Both enzymes displayed only detectable $\Delta^9$-18:0-ACP desaturase activity. In addition to catalyzing a similar activity, these mutants share a 50 residue region of overlap (residues 178–227) of the $\Delta^9$-18:0-ACP desaturase.

This suggested that determinants of chain-length and double bond positional specificities are present in this portion of the $\Delta^9$-18:0-ACP desaturase. Thus, a third chimera was constructed in which residues 172–221 of the $\Delta^6$-16:0-ACP desaturase were replaced with the corresponding 50 amino acid region from the $\Delta^9$-18:0-ACP desaturase. The resulting enzyme catalyzed the $\Delta^6$ or $\Delta^9$ desaturation of both 16:0-ACP and 18:0-ACP. A nearly identical activity was obtained for a fourth chimera, in which a 30 amino acid subset of this domain (residues 178–207 of the $\Delta^9$-18:0-ACP desaturase) was transposed into the $\Delta^6$-16:0-ACP desaturase. As shown in FIG. 1, in sharp contrast to the activity of the wild-type $\Delta^6$-16:0-ACP desaturase this enzyme catalyzed $\Delta^6$ and $\Delta^9$ desaturation at a ratio of nearly 3:1 and 1:1 with 16:0-ACP and 18:0-ACP, respectively. Moreover, the specific activity with 18:0-ACP as a substrate was nearly twice that detected with 16:0-ACP. These results are in sharp contrast to the activity of the wild-type $\Delta^6$-16:0-ACP desaturase. Though this chimeric enzyme is able to catalyze the insertion of a double bond at more than one position of 18:0-ACP, while the wild-type $\Delta^6$-16:0-ACP desaturase only has detectable $\Delta^6$ desaturase activity with 16:0-ACP. In addition, the wild-type enzyme was about 6-fold more active with 16:0-ACP than with 18:0-ACP.

To further characterize the 50 amino acid region of the $\Delta^9$-18:0-ACP desaturase, a smaller portion of this sequence (residues 178–202) was transposed into the $\Delta^6$-16:0-ACP desaturase (a fifth chimera). Unlike that of the wild-type $\Delta^6$-16:0-ACP desaturase, the specific activity of the resulting enzyme was nearly equal with 16:0- and 18:0-ACP. In addition to a broadened fatty acid chain-length specificity, the mutant desaturase catalyzed the insertion of a double bond almost exclusively at the $\Delta^6$ position of 16:0- and 18:0-ACP. Furthermore, the specific activity of this enzyme was more than two-fold greater than that of the wild-type $\Delta^6$-16:0-ACP desaturase. This may in part reflect the greater stability of the mutant enzyme in *E. coli* (i.e., the mutant desaturase was expressed to higher levels and displayed greater solubility than the wild-type $\Delta^6$-16:0-ACP desaturase).

Region 178–207 of the $\Delta^9$-18:0-ACP desaturase contains nine amino acids that are different from those found in the analogous portion of the $\Delta^6$-16:0-ACP desaturase. Through site-directed mutagenesis of the $\Delta^6$-16:0-ACP desaturase, each of these residues, either individually or in combination, was converted to that present in the $\Delta^9$-18:0-ACP desaturase. An activity qualitatively similar to that of the fourth chimera was obtained by the following mutation of the $\Delta^6$-16:0-ACP desaturase: A181T/A188G/Y189F/S205N/L206T/G207A. (Note: Amino acid numbering is given with respect to the $\Delta^9$-18:0-ACP desaturase.) In addition, the fifth chimera phenotype (i.e., broadened chain-length specificity) was achieved qualitatively by the mutation A188G/Y189F of the $\Delta^6$-16:0-ACP desaturase. Mutant desaturases with unexpected activities were also obtained in these experiments. For example, the mutation A181T/A200F of the $\Delta^6$-16:0-ACP desaturase gave rise to an enzyme that catalyzed primarily the $\Delta^9$ desaturation of 18:0-ACP, but functioned as a $\Delta^6$ desaturase with 16:0-ACP. The specific activity of this enzyme with 18:0-ACP, however, was about 3-fold less than that detected with 16:0-ACP. Furthermore, the mutation A181T/A200F/S205N/L206T/G207A of the $\Delta^6$-16:0-ACP desaturase yielded an enzyme that possessed only detectable $\Delta^9$ desaturase activity with 18:0-ACP and was nearly four-fold more active with this substrate than with 16:0-ACP. Like mutant A181T/A200F, this enzyme retained $\Delta^6$ desaturase activity with 16:0-ACP.

Changes in the substrate binding properties of these enzymes can be discounted as an underlying cause of the observed effects because their values are not significantly different from those of the wild type enzyme. The Km values for the wild-type $\Delta^6$-16:0-ACP desaturase, the fifth chimera, and mutant 188G/Y189F were estimated to be in the range of 0.2 to 0.6 $\mu$M for both 16:0- and 18:0-ACP.

As described in Example 1, the crystal structure of castor $\Delta^9$-18:0-ACP desaturase was determined making it possible to interpret the results on chimeras and mutants in light of the arrangement of the active site. The subunit structure contains a very deep and narrow channel which appears to correspond to the binding site for the stearic acid part of the substrate. The form of the channel imposes a bent conformation of the aliphatic chain at the point where the double bond is introduced, between carbon 9 and 10, corresponding to the cis configuration of the oleic acid product, positioning the potential double bond rather close to the catalytic iron center in the subunit. This substrate binding channel thus sets severe restrictions on the length of the aliphatic chain beyond the introduced double bond which can in part explain the differences in specificity for the enzymes in this family. As can be seen, variants of the enzyme which accept substrates with fewer carbon atoms beyond the double bond, have their binding clefts closed by substitutions of amino acid with bulkier side chains. The amino acids involved in determining the specificity in this part of the binding site are 114–115, 117–118, 179, 181 and 188–189.

In the absence of a structural model for the enzyme-substrate-ACP complex, the determinants of chain length specificities on the other side of the double bond, towards the acyl carrier protein are not as straightforward to deduce. Assuming that ACP binds in the same way in the different enzymes of this kind, differences in the amino acid side chains in the upper part of the substrate channel and at the entrance at the surface of the subunit would allow the enzymes to accommodate different lengths of the alkyl chain between the double bond and the phosphopantheine prosthetic group of ACP. However, the amino acids lining the upper part of the binding site, from the double bond to the surface of the protein are conserved in the available enzyme sequences and determinants for specificity are most likely to be found at the entrance of the substrate channel and at the enzyme surface which interacts with acyl-ACP. Here the binding pocket widens and it has not been possible to model the phosphopantheine part the stearoyl-ACP. Residues 280, 283, 286 and 294 in this area are not conserved between the different enzymes and might be involved in determining the substrate specificity.

From the structure of the binding site in this area it is possible to rationalize some of the results on chimeras and mutants. All the chimeras and mutants involve the determinant 179–189 (actually residues 179, 181, 188–189) and it is thus not surprising to find effects on specificity. Both the first and second chimeras have very little residual activity, probably due to some steric clashes upon their formation. The first chimera has this determinant of $\Delta^9$-18:0 ACP desaturase in the deep pocket and also the surface determinant specific for of $\Delta^9$-18:0 ACP desaturase, only one determinant, residues 114–115 and 117–118 specific for of $\Delta^6$-16:0 ACP desaturase and thus the remaining activity of this chimera is that of a $\Delta^9$-18:0 ACP desaturase. The second chimera has the whole determinant of $\Delta^9$-18:0 ACP desaturase in the area of the buried pocket and the known determinant of $\Delta^6$-16:0 ACP desaturase at the surface end; this chimera also has $\Delta^9$-18:0 ACP activity. The third and forth chimeras have retained their activity, one of the determinants in the deep pocket is that for a $\Delta^9$-18:0 ACP, residue A181 is substituted for the larger threonine side chain but at the same time A188 is substituted for glycine and Y189 for phenylalanine, actually making more space available in the deep cavity and thus allowing even for $\Delta^6$-18:0 ACP activity. The fifth chimera differs from the fourth chimera only in that it has retained the $\Delta^6$-16:0 ACP desaturase sequence for residues 203–207. These residues are at the upper part of the substrate channel but do not make direct contact to the substrates and it is difficult to understand the effect on the substrate specificity. These residues are fairly conserved between the known desaturases in this family, only $\Delta^6$-16:0 ACP desaturase has a different sequence for residue 205 to 207, and this region probably does not constitute part of the natural determinant for substrate specificity. In the case of mutant A181T/A200F the decrease in the $\Delta^6$-16:0 ACP activity compared to the wild type enzyme is consistent with the structural changes in the substrate channel due to a decrease in size of this cavity by changing A181 to threonine. The effect of A200F is not possible to rationalize, this residue is on the surface of the subunit pointing away from the substrate-channel. In all sequenced desaturases in this family except $\Delta^6$-16:0 ACP this residue is a phenylalanine. From the foregoing discussion it is clear that the activity of A181T/A200F/S205N/L206T/G207A is impossible to explain in structural terms, we can not rationalize the effects of changes at residues 200 and 205–207.

Thus, it has been shown that regio- and chain length specificities of fatty acid desaturase can be changed by specific amino acid replacements. The determinants for chain length specificity partly map onto the region of the three-dimensional structure which define shape and size of the substrate binding channel. However, some of these residues lie outside the substrate binding channel and changes in such residues may result in new and useful activities. With the availability of the three-dimensional structure of fatty acid ACP desaturase, the successful attempts to change the substrate specificities presented here can now be extended to rationally designed variants of the enzyme possessing different chain length- as well as regio-specificities. However, this will be successful only if we, from the crystal structure of a substrate complex and the availability of multiple amino acid sequences of enzymes in this family, can resolve what are the determinants for specificity at the entrance of the substrate channel.

Materials and Methods

Fatty acid names are abbreviated in the format x:ydz where x is the chain-length or numbers of carbon atoms in the fatty acid, y is the number of double bonds, and z is the position of the double bond in the fatty acid relative to the carboxyl end of the molecule (e.g., oleic acid or 18:1$\Delta^9$ is an 18 carbon fatty acid with one double bond, which is positioned at the ninth carbon atom relative to the carboxyl end of the molecule).

Preparation of Chimeric Mutants

Chimeric mutants were prepared by linking portions of the coding sequence of the mature T. alata $\Delta^6$-16:0- and $\Delta^9$-18:0-ACP desaturases via native restriction enzyme sites or restriction enzyme sites generated by PCR. Site-specific mutations in the coding sequence of amino acids 178–202 of the $\Delta^9$-18:0-ACP desaturase (equivalent to residues 172–196 of the $\Delta^6$-16:0-ACP desaturase) were introduced by extension and amplification of overlapping oligonucleotide primers using PCR with Pfu polymerase (Stratagene). Mutations A181T/A188G/Y189F were made with the following oligonucleotides: 5'ATGGATCCTGGCACGGATAACAAC-CCGTAC3' (Primer 1A); 5'ACGAGGTGTAGATAAATC-CGAGGTACGGGTTGTTATCCG3' (Primer 2A); 5'TATCTACACCTCGTATCAGGAGAGGGCGACA3' (Primer 3A); 5'TTGAATTCCATGGGAAATCGCT-GTCGCCCTCTCCTG3' (Primer 4A). Mutations A188G/Y189F were introduced using the following oligonucleotides: 5'ATGGATCCTGGCGCGGATAACAA-CCCGTAC3' (Primer 1 B); Primer 2A; Primer 3A; Primer 4A. Mutations A181T/A200F were generated with the following: Primer 1A; 5'ACGAGGTGTAGATATATGCGAG-GTACGGGTTGTTATCCG3' (Primer 2B); Primer 3A; 5'TTGAATTCCATGGGAAATGAATGTCGC-CCTCTCCTG3' (Primer 4B). PCR reactions were conducted without added template using 12.5 pmoles of Primers 1A or B and 4A or B and 6.25 pmoles of Primers 2A or B and 3A. For the first 10 PCR cycles, an annealing temperature of 37° C. and an extension temperature of 72° C. were used. This was followed by an additional 20 cycles with the annealing temperature increased to 55° C. Products from PCR reactions were digested with BamHI and EcoRI and inserted into the corresponding sites of pBluescript II KS(-) (Stratagene) from which the nucleotide sequence was determined using a Sequenase 2.0 kit (Amersham). This plasmid was then digested with BamHI and EcoRI and the recovered insert was ligated to the coding sequence of amino acids 1–171 of the mature $\Delta^6$-16:0-ACP desaturase in the expression vector pET3a (Novagen). The resulting construct (now containing the coding sequence of amino acids 1–196 of mutant or wild-type $\Delta^6$-16:0-ACP desaturase) was restricted with NcoI and EcoRI and ligated to an NcoI/EcoRI fragment containing the coding sequence of the remaining amino acids (residues 197–355) of the $\Delta^6$-16:0-ACP desaturase and a portion of the pET3d plasmid (nucleotides). The mutation S205N/L206T/G207A was generated by PCR amplification of the coding sequence of amino acids 197–355 of the $\Delta^6$-16:0-ACP desaturase using as template the original cDNA for this enzyme in pBluescript SK(-). The 5' oligonucleotide (5'TTTCCATGGGAACACGGCTC-GGCTAGCGAGGCAGAAGG3'), contained the appropriate mutant codons, and the T7 primer was used as the 3' oligonucleotide for PCR reactions. The amplification product was digested with NcoI and BclI and inserted into the NcoI/BamHI site of pET 3d. A NcoI/EcoRI fragment from this construct was then ligated to the coding sequence of amino acids 1–196 of the appropriate mutant $\Delta^6$-16:0-ACP desaturase (e.g. A181T/A200F) to generate a full-length coding sequence. Products of PCR reactions were sequenced to confirm the presence of desired mutations.

Production of acyl-ACP Desaturases

Wild-type and mutant acyl-ACP desaturases were obtained by expression of the coding sequences in E. coli BL21 (DE3) behind the T7 RNA polymerase promoter using the vectors pET3a or pET3d. Recombinant enzymes whose activities are described in FIG. 1 were purified from 6 to 9 liter bacterial cultures induced at 20° to 25° C. Protein purification was performed using DEAE-anionic exchange chromatography followed by 20HS (Perseptive Biosystems) cationic exchange chromatography using a Biocad Sprint HPLC (Perseptive Biosystems). Mutant desaturases were obtained at r 90% purity, and the wild-type $\Delta^6$-16:0-ACP desaturase was recovered at approximately 80% purity. Following purification, enzymes were exchanged into a buffer consisting of 40 mM Tris-HCl (pH 7.5), 40 mM NaCl, and 10% glycerol and stored in aliquots at −75° C. after flash-freezing in liquid nitrogen.

Assay and Analysis of acyl-ACP Desaturases

Acyl-ACP desaturation assays and analysis of reaction products were conducted as previously described (Cahoon, E. B., et al., Proc. Nat. Acad. Sci., USA. 89:1184, (1994)) with the following modifications: recombinant Anaebena vegetative ferredoxin (22 fg/assay) and maize root FNR (0.4 U/assay) were used in place of spinach ferredoxin and FNR and amounts of NADPH and [1–14C}16:0- or 18:0-ACP per assay were increased to 2.5 mM and 178 pmoles (or 1.2 fM), respectively. ACP used in the synthesis of substrates was recombinant spinach ACP-I. The specific activity of [1–14C}16:0 and 18:0 (American Radiolabeled Chemicals) was 55 mCi/mmol. Enzyme activity was measured by determining the percentage of monounsaturated product generated in desaturation assays. The distribution of radioactivity between products and unreacted substrate was measured from phosphor images of argentation TLC separations using ImageQuant software and by liquid scintillation counting of TLC scrapings.

Determination of Double Bond Positions

Double bond positions of monounsaturated fatty acid products were determined by the mobility of methyl ester derivatives on 15% argentation TLC plates and by GC-MS analysis of dimethyl disulfide adducts of these derivatives. Desaturation assays for GC-MS analyses were conducted using unlabeled 16:0-, 17:0-, and 18:0-ACP as substrates and purified enzymes. In addition to results presented in the text, about 15% of the desaturation products formed by the reaction of 17:0-ACP with the wild-type $\Delta^6$-16:0-ACP desaturase was detected as the 17:1$\Delta^7$ isomer. The remainder of the product was 17:1$\Delta^6$ with trace amounts of 17:1$\Delta^9$ also detected.

EXAMPLE 3

Results and Discussion

Mutant acyl-ACP desaturases with altered activities

The studies described here were initiated prior to the availability of three-dimensional data from the crystal structure of the castor $\Delta^9$-18:0-ACP desaturase (Lindqvist et al., (1996) EMBO J. 15, 4081–4092). In the absence of this information, efforts were made to understand the structural basis for differences in activities catalyzed by a $\Delta^6$-16:0-ACP desaturase and a $\Delta^9$-18:0-ACP desaturase by generating a series of chimeric enzymes that combined portions of these two desaturases (e.g., see FIG. 2). The activities of the resulting enzymes were then assessed to determine the effect on their substrate and regio-specifities. In this manner, a 30-amino acid domain encompassing residues 178–207 of the $\Delta^9$-18:0-ACP desaturase was identified that contained determinants of both chain-length and double bond positional specificities. When this domain was introduced in place of the analogous portion of the $\Delta^6$-16:0-ACP desaturase (FIG. 2), the resulting enzyme (designated Chimera 1 of Example 3) displayed a mixture of $\Delta^6$ and $\Delta^9$ desaturase activities with 16:0- and 18:0-ACP (Table 1). In sharp contrast to the wild type $\Delta^6$-16:0-ACP desaturese, Chimera 1 of Example 3 catalyzed $\Delta^6$ and $\Delta^9$ desaturation with 16:0-ACP at a ratio of 3:1 and with 18:0-ACP at a ratio of 1:1 (Table 1). In addition, the specific activity of Chimera 1 of Example 3 with 18:0-ACP was twice that detected with 16:0-ACP (Table 1).

It should be noted that the chimeras discussed in Example 3 were also described in Example 2. The chimera numbers assigned in the Exemplification section are example-specific. Thus, for example, chimera 1 of Example 3 is referred to as "a fourth chimera" in Example 2.

ACP desaturase. An activity qualitatively similar to that of Chimera 1 of Example 3 was obtained by the following mutation of the $\Delta^6$-16:0-ACP desaturase: A181T/A188G/Y189F/S205N/L206T/G207A (Table 1). In addition, the Chimera 2 of Example 3 phenotype (i.e., broadened fatty acid chain-length specificity) was achieved qualitatively by the mutation A188G/Y189F of the $\Delta^6$-16:0-ACP desaturase (Table 1).

Mutant desaturases with unexpected activities were also generated in these experiments. For example, the mutation A181T/A200F of the $\Delta^6$-16:0-ACP desaturase gave rise to an enzyme that catalyzed primarily the $\Delta^9$ desaturation of

TABLE 1

Specific activities of wild type and mutant $\Delta^6$-16:0-ACP desaturases with 16:0- or 18:0-ACP*

| | Specific activity (nmole/min/mg protein) | | | | Ratio of Total |
|---|---|---|---|---|---|
| | 16:0-ACP | | 18:0-ACP | | Specific Activity |
| Enzyme* | $\Delta^6$ | $\Delta^9$ | $\Delta^6$ | $\Delta^9$ | 16:0-ACP:18:0-ACP |
| $\Delta^6$-16:0-ACP Desaturase (wild type) | 100 ± 3 | n.d.† | 11 ± 1 (2:1‡) | 5.5 ± 0.2 | 6:1 |
| Chimera 1 ($\Delta^6/\Delta^9_{178-207}/\Delta^6$) | 13 (3:1) | 4.0 | 15 (1:1) | 17 | 1:2 |
| Chimera 2 ($\Delta^6/\Delta^9_{178-202}/\Delta^6$) | 227 ± 25 | ND | 253 ± 25 (50:1) | 5.3 ± 0.5 | 1:1 |
| A181T/A188G/Y189F/S205N/L206T/G207A§ | 33 ± 4 (3:1) | 12 ± 1 | 31 ± 2 (1:2) | 53 ± 5 | 1:2 |
| A188G/Y189F | 34 ± 3 | ND | 34 ± 4 (50:1) | 0.7 ± 0.1 | 1:1 |
| A181T/A200F | 149 | ND | 3.1 (1:15) | 44 | 3:1 |
| A181T/A200F/S205N/L206T/G207A | 19 ± 1 (14:1) | 1.4 ± 0.3 | ND | 76 ± 5 | 1:4 |

Shown are $\Delta^6$ and $\Delta^9$ desaturase activities with each substrate ± S.D. of three independent measurements.
*In addition to results presented in Table 1, approximately 15% of the desaturation products formed by the reaction of 17:0-ACP with the wild type $\Delta^6$-16:0- ACP desaturase was detected by GC-MS as the 17:1 $\Delta^7$ isomer. The remainder of the product was 17:1 $\Delta^6$ with trace amounts of 17:1 $\Delta^9$ also detected. Small amounts of $\Delta^7$ isomers were also present in mass spectra of products formed from 16:0- and 18:0-ACP with the wild type $\Delta^6$-16:0-ACP desaturase and several of the mutants. These accounted for <5% of the total products. No $\Delta^8$ isomers were detected in mass spectra of desaturation products.
†n.d. = not detected.
‡x:y is the ratio of $\Delta^6$:$\Delta^9$ activity with the given substrate.
§Amino acid numbering corresponds to the sequence of the mature $\Delta^9$-18:0-ACP desaturase.

An additional novel activity was obtained using a smaller portion of the 30-amino acid domain described above. When residues 178–202 of the $\Delta^9$-18:0-ACP desaturase were introduced in place of the corresponding portion of the $\Delta^6$-16:0-ACP desaturase, an enzyme that functioned almost exclusively as a $\Delta^6$ desaturase with 16:0- and 18:0-ACP was obtained (designated Chimera 2 of Example 3; Table 1). The double bond positional specificity with 18:0-ACP was distinctly different than that of the wild type $\Delta^6$-16:0-ACP desaturase which displayed mixed $\Delta^6$ and $\Delta^9$ desaturase activity with this substrate. In addition, Chimera 2 of Example 3, unlike the wild type enzyme, was almost equally active with 16:0- and 18:0-ACP (Table 1). Interestingly, the specific activity of Chimera 2 of Example 3 with 16:0-ACP was two-fold greater than that detected with the wild type $\Delta^6$-16:0-ACP desaturase. Also, the specific activity with 18:0-ACP was more than 15-fold greater than that displayed by the wild type enzyme.

Amino acids 178–207 of the $\Delta^9$-18:0-ACP desaturase contain nine residues that are different from those found in the equivalent portion of the $\Delta^6$-16:0-ACP desaturase (FIG. 2). Through site-directed mutagenesis of the $\Delta^6$-16:0-ACP desaturase, each of these residues, either individually or in combination, was converted to that present in the $\Delta^9$-18:0-

18:0-ACP, but functioned as a $\Delta^6$ desaturase with 16:0-ACP (Table 1). Furthermore, the mutation A181T/A200F/S205N/L206T/G207A of the $\Delta^6$-16:0-ACP desaturase yielded an enzyme that functioned primarily as a $\Delta^9$-18:0-ACP desaturase. This enzyme displayed only $\Delta^9$ desaturase activity with 18:0-ACP and was nearly four-fold more active with this substrate than with 16:0-ACP (Table 1). However, like mutant A181T/A200F, this enzyme retained $\Delta^6$ desaturase activity with 16:0-ACP.

Of note, the enzyme assay used in these studies precluded the collection of large amounts of kinetic data. However, $K_m$ values determined for the wild type $\Delta^6$-16:0-ACP desaturase, Chimera 2 of Example 3, and mutant A188G/Y189F were in the range of 0.2 to 0.6 μM with both 16:0- and 18:0-ACP, suggesting that, at least in the case of these enzymes, changes in the substrate binding properties can be discounted as an underlying cause of differences in activities.

Interpretation of mutant enzymes in terms of the crystal structure of the $\Delta^9$-18:0-ACP desaturase Recently, the crystal structure of castor $\Delta^9$-18:0-ACP desaturase was determined (Lindqvist et al., (1996) *EMBO J.* 15, 4081–4092), making it possible to interpret a portion of the above results in terms of the arrangement of the active site. The subunit structure of the $\Delta^9$-18:0-ACP desaturase contains a catalytic di-iron cluster, which represents a fixed point for the introduction of the double bond. Adjacent to the iron atoms is a deep and narrow channel that likely represents the binding pocket for the stearic acid (18:0) portion of the substrate. The channel imposes a bent conformation on the fatty acid chain between carbon atoms 9 and 10, the site of desaturation. This conformation corresponds to the cis configuration of the oleoyl (18:1$\Delta^9$)-ACP product and positions the location of double bond insertion close to the di-iron center. In this model, the architecture of the fatty acid binding channel in relation to the catalytic iron cluster affects both substrate specificity and the position at which double bonds are introduced.

With regard to substrate specificity of acyl-ACP desaturases, the geometry of the lower portion of the binding pocket places severe constraints on the length of the acyl chain that can be accommodated beyond the point where the double is to be introduced. As such, residues at the bottom of the substrate channel are likely the most critical for determining fatty acid chain-length specificity. This explains the functional properties of Chimera 2 of Example 3 and mutant A188G/Y189F which display increased $\Delta^6$ desaturase activity with 18:0-ACP compared to the wild type $\Delta^6$-16:0-ACP desaturase. Based on the model of the active site, substitution of alanine 188 for a smaller glycine and tyrosine 189 for phenylalanine extends the cavity at the bottom of the active site enough to accommodate the two additional carbon atoms at the methyl end of 18:0-ACP. As a result, Chimera 2 of Example 3 and mutant A188G/Y189F are able desaturate 18:0-ACP with a rate comparable to that observed with 16:0-ACP.

More difficult to interpret are alterations in the double bond positional specificities of mutants described above. This class of fatty acid desaturases inserts a double bonds at a characteristic position from the carboxyl end of acyl chains (Cahoon and Ohlrogge, (1994) *Plant Physiol.* 104, 827–844; and Gibson, (1993) *Biochim. Biophys. Acta* 1169, 231–235). Thus, the site of double bond insertion by acyl-ACP desaturases is likely associated with interactions between the upper part of the active site and the ACP portion of substrates. Assuming that ACP binds in the same manner in all acyl-ACP desaturases, differences in the amino acid side chains at the enzyme surface and/or those lining the upper portion of the substrate binding channel would allow the enzyme to accommodate different lengths of the fatty acid chain between the site of double bond insertion and the thioester linkage to ACP. However, in the absence of a crystal structure of the desaturase that includes a bound acyl-ACP substrate, it is not possible to interpret differences in double bond positional specifities of the mutants described above or in naturally occurring enzymes such as the $\Delta^4$- and the $\Delta^6$-16:0-ACP desaturases. Of the residues that contribute to altered double bond positional specificity in the mutants described above, alanine 200 is on the surface pointing away from the substrate channel and amino acids 205–207 are located outside of the active site. It is possible that these residues mediate changes in activity via subtle packing effects in the enzyme rather than through direct interactions with substrates, as has been reported for mutants of serine proteases with altered function (Hedstrom, (1994) *Curr. Opin. Struct. Biol.* 4, 608–611; and Schellenberger et al., (1993) *Biochemistry* 32, 4349–4353).

Modelling of the active sites of variant acyl-ACP desaturases

The crystallographic model of the active site of the castor $\Delta^9$-18:0-ACP desaturase also provides useful information regarding the fatty acid chain-length specifities of naturally-occurring variant acyl-ACP desaturases (e.g., the $\Delta^9$-14:0-, $\Delta^4$-16:0-, and $\Delta^6$-16:0-ACP desaturases). Variant desaturases that accept substrates with fewer carbon atoms in the distal portion of the active site (i.e., the region beyond the site of double insertion) have their binding clefts occluded by substitutions of amino acids with bulkier side chains. The amino acids involved in determining the specificity in this part of the binding site are: 114–115, 117–118, 179, 181, and 188–189. For example, the $\Delta^9$-18:0-ACP desaturase, which accepts nine carbon atoms of the fatty acid substrate beyond the point of double bond insertion, contains a methionine, proline, and glycine at amino acid positions 114, 179, and 188, respectively. In contrast, the $\Delta^9$-14:0-ACP desaturase, which accepts five carbon atoms of the substrate in the deep portion of the active site, contains the larger hydrophobic residues leucine, isoleucine, and leucine at positions 114, 179, and 188, respectively. Such amino acid differences likely contribute to a smaller binding pocket in the $\Delta^9$-14:0-ACP desaturase relative to the $\Delta^9$-18:0-ACP desaturase.

Rational design of acyl-ACP desaturase activities

Residues described above that line the lower portion of the active site represent potential targets for the rational design of acyl-ACP desaturase activities with respect to fatty acid chain-length specificity. As a test of this, leucine 118 and proline 179 of the mature castor $\Delta^9$-18:0-ACP desaturase were replaced with the bulkier residues phenylalanine and isoleucine, respectively. Consistent with the proposed model of the active site, these substitutions yielded an enzyme that was functionally converted from a $\Delta^9$-18:0-ACP desaturase to a $\Delta^9$-16:0-ACP desaturase. The altered activity resulted both from a reduction in the specific activity with 18:0-ACP and an increase in the specific activity with 16:0-ACP. Overall, the specific activity of the L 118F/P179I mutant with 16:0-ACP was more than 15-fold greater than that displayed by the wild type $\Delta^9$-18:0-ACP desaturase with this substrate. GC-MS analyses of desaturation products indicated that the $\Delta^9$ position was the exclusive site of double bond insertion when the mutant was presented with 16:0-ACP. However, when 18:0-ACP was provided as a substrate, not only was 18:1$\Delta^9$ formed, but approximately 5% of the desaturation products were detected as the $\Delta^{10}$ isomer. This is consistent with a reduced ability of the binding pocket of the L118F/P179I mutant to accommodate the longer acyl chain of the 18:0-ACP substrate.

Overall, these results demonstrate the ability to modify the substrate and double bond positional specificities of acyl-ACP desaturases using amino acid sequence alignments either alone or in conjunction with three-dimensional structural data from the castor $\Delta^9$-18:0-ACP desaturase. These two approaches provided unique and complementary information with regard to understanding the molecular mechanisms of the substrate and regio-specificities displayed by acyl-ACP desaturases. In addition, several of the mutants described here have possible biotechnological applications. For example, Chimera 2 of Example 3 or the $\Delta^6$-16:0-ACP desaturase mutant A188G/Y189F provides a means of producing petroselinic acid (18:1$\Delta^6$) in transgenic crop plants. This fatty acid is useful in the production of low-caloric margarine and as a precursor of adipic acid for the manufacture of nylon 66 (Murphy, (1992) *Trends Biotechnol.* 10, 84–87; and Ohlrogge, (1994) *Plant Physiol.* 104, 821–826).

Also, the rationally designed L118F/P179I mutant of the castor $\Delta^9$-18:0-ACP desaturase may be useful in enhancing the unsaturated fatty acid quality of vegetable oils through the reduction of palmitic acid (16:0) content. These results along with additional information from crystallographic studies of acyl-ACP desaturases will lead to the continued design of enzymes for the production of novel monounsaturated fatty acids in transgenic oilseed crops.

Material and Methods

Preparation of chimeric enzymes and site-directed mutants of the $\Delta^6$-16:0-ACP desaturase Chimeric enzymes were prepared by linking portions of the coding sequence of the mature *T. alata* $\Delta^9$-18:0- and $\Delta^6$-16:0-ACP desaturases via native restriction enzyme sites or restriction sites generated by PCR. The coding sequences used were derived from the previously described cDNAs pTAD2 (Cahoon et al., (1994) *Plant Physiol.* 106, 807–808) and pTAD4 (Cahoon et al., (1994) *J. Biol. Chem.* 269, 27519–27526). Site-specific mutations in the coding sequence of amino acids 178–202 of the mature $\Delta^9$-18:0-ACP desaturase (equivalent to residues 172–196 of the $\Delta^6$-16:0-ACP desaturase) were introduced by extension and amplification of overlapping oligonucleotide primers using PCR with Pfu polymerase (Stratagene). As an example, mutations A188G/Y189F were made with the following oligonucleotides (base changes are indicated in upper case): 5'atggatcctggcacggataacaacccgtac3' (Primer 1); 5'acgaggtg-tagataAatCcgaggtacgggttgttatccg3' (Primer 2); 5'tatctacac-ctcgtatcaggagagggcgaca3' (Primer 3); 5'ttgaattccatgg-gaaatcgctgtcgccctctcctg3' (Primer 4). PCR reactions were conducted without added template using 12.5 pmoles of Primers 1 and 4 and 6.25 pmoles of Primers 2 and 3 in 50 $\mu$l reactions. For the first 10 PCR cycles, an annealing temperature of 37° C. and an extension temperature of 72° C. were used. This was followed by an additional 20 cycles with the annealing temperature increased to 55° C. Other mutations in the region of amino acids 178–202 were generated using a similar combination of primers containing coding sequence of the wild type enzyme or that of the desired mutation. PCR products were linked at their 5' and 3' ends to the coding sequence of amino acids 1–171 and 197–355 of the wild type $\Delta^6$-16:0-ACP desaturase via 5' BamHI and 3' NcoI sites and assembled into the bacterial expression vector pET3d (Novagen). The mutation S205N/L206T/G207A was generated by PCR amplification of the coding sequence of amino acids 197–355 of the $\Delta^6$-16:0-ACP desaturase using as template a cDNA for this enzyme in pBluescript II SK(–) (Jaworski and Stumpf (1974) *Arch. Biochem. Biophys.* 162, 158–165). The 5' oligonucleotide (5'tttccatgggaACACggCTcggctagcgaggcagaagg3') contained the appropriate mutant codons (shown in upper case), and the T7 primer was used as the 3' oligonucleotide for PCR reactions. The amplification product was digested with NcoI and BclI and inserted into the NcoI/BamHI site of pET3d. A NcoI/EcoRI fragment from this construct was then ligated to the coding sequence of amino acids 1–196 of wild type or mutant $\Delta^6$-16:0-ACP desaturases (e.g., A181T/A200F) to generate a full-length coding sequence. All PCR generated DNA was sequenced using a Sequenase 2.0 kit (Amersham) to confirm the presence of desired mutations and the absence of any secondary mutations.

Preparation of site-directed mutants of the castor $\Delta^9$-18:0-ACP desaturase Mutations L118F and P179I were introduced sequentially into the castor $\Delta^9$-18:0-ACP desaturase. The mutation L118F was generated by overlap extension PCR (Ho et al., (1989) *Gene* 77, 51–59) using the coding sequence of the mature wild type castor $\Delta^9$-18:0-ACP desaturase in the vector pET9d (Novagen) as the template. Two separate PCR reactions were conducted using the primer pairs (base changes are shown in upper case): (a) T7 primer and 5'ccgaactccatcGaaggtattcagca3' and (b) 5'tgctgaataccttC-gatggagttcgg3' and 5'gcaaaagccaaaacggtaccatcaggatca3' (Primer A). The agarose gel-purified products of the two reactions were combined and amplified together with the T7 primer and Primer A. The product of this reaction containing the mutation for L118F was digested with XbaI and BamHI and inserted in place of the corresponding portion of the wild type castor $\Delta^9$-18:0-ACP desaturase in the vector pET9d.

The double mutant L118F/P179I was generated as described above using the coding sequence of the mutant L118F in pET9d as template and the primer pairs (base changes in upper case): (a) T7 primer and 5'ggactgttttctgtc-cgAATatccattcctgaacca3' and (b) 5'tggttcaggaatggatATTcg-gacagaaaacagtcc3' and Primer A. The product generated following two rounds of PCR was digested with XbaI and PstI and inserted in place of the corresponding portion of the wild type castor $\Delta^9$-18:0-ACP desaturase in vector pET9d.

Expression and purification of acyl-ACP desaturases

Wild type and mutant acyl-ACP desaturases were obtained by expression of the coding sequences in *Escherichia coli* BL21 (DE3) behind the T7 RNA polymerase promoter using pET expression vectors (Novagen) as described above. Recombinant enzymes whose activities are described in Table 1 were purified from extracts of six to nine liter bacterial cultures induced at 22° C. (or at 30° C., in the case of the wild type castor $\Delta^9$-18:0-ACP desaturase and mutant L118F/P179I). Protein purification was performed using DEAE-anion exchange chromatography followed by perfusion cation exchange chromatography using a 20 HS column (PerSeptive Biosystems). Mutant desaturases were obtained at 90% purity, and the wild-type $\Delta^6$-16:0-ACP desaturase was recovered at approximately 80% purity as determined by SDS-PAGE with Coomassie staining. The wild-type castor $\Delta^9$-18:0-ACP desaturase and mutant L118F/P179I were enriched to >90% purity using only 20 HS perfusion cation exchange chromatography. Following purification, enzymes were exchanged into a buffer consisting of 40 mM Tris-HCl (pH 7.5), 40 mM NaCl, and 10% glycerol and stored in aliquots at –75° C.

Enzyme assays

Acyl-ACP desaturation assays and analysis of reaction products were conducted as previously described (Cahoon et al., (1994) *J. Biol. Chem.* 269, 27519–27526) with the following modifications: recombinant Anabaena vegetative ferredoxin (22 $\mu$g/assay) and maize root ferredoxin-NADP$^+$ oxidoreductase (FNR) (0.4 U/assay) were used in place of spinach ferredoxin and FNR, and concentrations of NADPH and [1–$^4$C]16:0- or 18:0-ACP per assay were increased to 2.5 mM and 1.2 $\mu$M, respectively. Acyl-ACPs were synthesized enzymatically (using recombinant spinach ACP-I. Products and unreacted substrates were separated by argentation thin layer chromatography (TLC) as methyl ester derivatives (Cahoon and Ohlrogge, (1994) *Plant Physiol.* 104, 827–844; Cahoon et al., (1994) *J. Biol. Chem.* 269, 27519–27526; and Morris et al., (1967) *J. Chromatography* 31, 69–76), and the distribution of radioactivity between these moieties was measured by phosphor imaging of TLC plates using ImageQuant software (Molecular Dynamics) and by liquid scintillation counting of TLC scrapings.

Determination of double bond positions

Double bond positions of monounsaturated fatty acid products were determined by the mobility of methyl ester derivatives on 15% argentation TLC plates (Cahoon and Ohlrogge, (1994) *Plant Physiol.* 104, 827–844; and Morris et al., (1967) *J. Chromatography* 31, 69–76) and by gas chromatography-mass spectrometry (GC-MS) of dimethyl disulfide adducts of these derivatives (Cahoon et al., (1992)

Proc. Natl. Acad. Sci. U.S.A. 89, 11184–11188; Cahoon et al., (1994) J. Biol. Chem. 269, 27519–27526; and Yamamoto et al., (1991) Chem. Phys. Lipids 60, 39–50). Desaturation assays for GC-MS analyses were conducted using radiolabelled 16:0- and 18:0-ACP and unlabelled 17:0-ACP as substrates for purified enzymes.

We claim:

1. A method for modifying the chain length and double bond positional specificities of a soluble plant fatty acid desaturase, the method comprising modifying amino acid contact residues in the substrate binding channel of the soluble fatty acid desaturase which contact the fatty acid.

2. The method of claim 1 wherein the soluble plant fatty acid desaturase is an acyl-ACP desaturase.

3. The method of claim 2 wherein the acyl-ACP desaturase is a $\Delta^9$ desaturase.

4. The method of claim 3 wherein the $\Delta^9$ desaturase is produced by a plant selected from the group consisting of *Thunbergia alata* or *Ricinus communis*.

5. The method of claim 4 wherein the amino acid contact residues are selected from the group consisting of residues corresponding to amino acids 114, 115, 117, 118, 179, 181, 188 and 189 of the *Richinus communis* $\Delta^9$ ACP desaturase.

6. A method for modifying the chain length and double bond positional specificities of an acyl-ACP desaturase, comprising:

a) providing the primary amino acid sequence of the acyl-ACP desaturase;

b) aligning the primary amino acid sequence of the acyl-ACP desaturase with the primary amino acid sequence of the *Ricinus communis* $\Delta^9$ desaturase for maximum sequence conservation;

c) constructing a 3-dimensional model for the acyl-ACP desaturase based on the sequence conservation with the *Ricinus communis* $\Delta^9$ desaturase;

d) identifying amino acid contact residues within the substrate binding channel of the structure modeled in step c); and e) generating a mutant acyl-ACP desaturase having modified chain length and double bond positional specificities by replacing one or more of the amino acid contact residues identified in step d) with another amino acid residue.

7. A mutant acyl-ACP desaturase which is characterized by modification of one or more amino acid contact residues in the substrate binding channel and the ability to catalyze desaturation of a first fatty acid and a second fatty acid, the first and second fatty acids differing in their chain length, the desaturation rates of both the first and second fatty acids differing by no more than about 4-fold.

8. The mutant acyl-ACP desaturase of claim 7 which contains a point mutation at an amino acid contact residue in the substrate binding channel.

9. The mutant acyl-ACP desaturase of claim 7 wherein the first fatty acid has a chain-length of 16:0 and the second fatty acid has a chain-length of 18:0.

10. A mutant acyl-ACP desaturase having an amino acid substitution at a contact residue within the substrate binding channel.

11. The mutant acyl-ACP desaturase of claim 10 which is characterized by changes in chain-length and double bond positional specificity as compared to the wild-type acyl-ACP desaturase counterpart.

12. The mutant acyl-ACP desaturase of claim 11 wherein the acyl-ACP desaturase is the $\Delta^9$ acyl-ACP desaturase and the contact residues within the substrate binding channel are selected from the group consisting of residues corresponding to amino acids 114, 115, 117, 118, 179, 181, 188 and 189 of the *Ricinus communis* $\Delta^9$ ACP desaturase.

13. The mutant of claim 12 wherein the $\Delta^9$ acyl-ACP desaturase is produced by mutagenizing nucleic acid cloned from *Thunbergia alata* or *Ricinus communis.*

14. A chimeric acyl-ACP desaturase which is characterized by modification of one or more amino acid contact residues in the substrate binding channel and the ability to catalyze desaturation of a first fatty acid and a second fatty acid, the first and second fatty acids differing in their chain length, the desaturation rates of both the first and second fatty acids differing by no more than about 4-fold.

15. The chimeric acyl-ACP desaturase of claim 14 comprising a $\Delta^6$-16:0 ACP desaturase in which amino acids corresponding to amino acids 172–201 of *Ricinus communis* $\Delta^6$-16:0 ACP desaturase are replaced with amino acids corresponding to amino acids 178–207 of the *Ricinus communis* $\Delta^9$-18:0 ACP desaturase from a $\Delta^9$-18:0 ACP desaturase.

16. The chimeric acyl-ACP desaturase of claim 14 comprising a $\Delta^6$-16:0 ACP desaturase in which amino acids corresponding to amino acids 172–196 of *Ricinus communis* $\Delta^6$-16:0 ACP desaturase are replaced with amino acids corresponding to amino acids 178–202 of the *Ricinus communis* $\Delta^9$-18:0 ACP desaturase from a $\Delta^9$-18:0 ACP desaturase.

17. The chimeric acyl-ACP desaturase of claim 14 comprising a $\Delta^6$-16:0 ACP desaturase in which amino acids corresponding to amino acids 176, 183, 184, 200, 201 and 202 of the *Ricinus communis* $\Delta^6$-16:0 ACP desaturase are replaced with amino acids corresponding to amino acids 181, 188, 189, 205, 206 and 207 of the *Ricinus communis* $\Delta^9$-18:0 ACP desaturase, respectively, from a $\Delta^9$-18:0 ACP desaturase.

18. The chimeric acyl-ACP desaturase of claim 14 comprising a $\Delta^6$ 16:0 ACP desaturase in which amino acids corresponding to amino acids 183 and 184 of the *Ricinus communis* $\Delta^6$-16:0 ACP desaturase are replaced with amino acids corresponding to amino acids 188 and 189 of the *Ricinus communis* $\Delta^9$-18:0 ACP desaturase, respectively, from a $\Delta^9$-18:0 ACP desaturase.

19. The chimeric acyl-ACP desaturase of claim 17 comprising a $\Delta^6$-16:0 ACP desaturase in which amino acids corresponding to amino acids 176 and 195 of the *Ricinus communis* $\Delta^6$-16:0 ACP desaturase are replaced with amino acids corresponding to amino acids 181 and 200 of the *Ricinus communis* $\Delta^9$-18:0 ACP desaturase, respectively, from a $\Delta^9$-18:0 ACP desaturase.

20. The chimeric acyl-ACP desaturase of claim 17 comprising a $\Delta^6$-16:0 ACP desaturase in which amino acids corresponding to amino acids 176, 195, 200, 201 and 202 of the *Ricinus communis* $\Delta^6$-16:0 ACP desaturase are replaced with amino acids corresponding to amino acids 181, 200, 205, 206 and 207 of the *Ricinus communis* $\Delta^9$-18:0 ACP desaturase, respectively, from a $\Delta^9$-18:0 ACP desaturase.

* * * * *